United States Patent [19]

Raleigh et al.

[11] Patent Number: 5,401,870
[45] Date of Patent: Mar. 28, 1995

[54] SILICONE POLYETHER ALKYL COPOLYMER SYNTHESIS

[75] Inventors: William J. Raleigh, Rensselaer; Raymond J. Thimineur, Scotia, both of N.Y.

[73] Assignee: General Electric Company, Waterford, N.Y.

[21] Appl. No.: 81,949

[22] Filed: Jun. 22, 1993

Related U.S. Application Data

[63] Continuation of Ser. No. 774,444, Oct. 10, 1991, abandoned.

[51] Int. Cl.$^6$ .............................. C07F 7/08; C07F 7/18
[52] U.S. Cl. .................................... 556/445; 556/446; 424/66; 424/65; 424/59; 424/60; 424/405
[58] Field of Search ................... 556/445, 446; 424/66, 424/65, 59, 60, 405

[56] References Cited

U.S. PATENT DOCUMENTS

| | | | |
|---|---|---|---|
| 3,172,899 | 3/1965 | Bailey | 556/445 |
| 3,560,544 | 2/1971 | Haluska | 556/445 X |
| 3,629,308 | 12/1971 | Bailey et al. | 556/445 |
| 4,218,250 | 8/1980 | Kasprzak | 106/3 |
| 4,265,878 | 5/1981 | Keil | 424/68 |
| 4,268,499 | 5/1981 | Keil | 424/68 |
| 4,311,695 | 1/1982 | Starch | 424/184 |
| 4,421,656 | 12/1983 | Donatelli et al. | 252/8.5 |
| 4,853,474 | 8/1989 | Bahr et al. | 556/445 |
| 4,980,156 | 12/1990 | Raleigh et al. | 424/66 |
| 4,988,504 | 1/1991 | Zotto et al. | 424/65 |
| 5,001,248 | 3/1991 | Grabowski | 556/445 X |
| 5,004,559 | 4/1991 | Koerner et al. | 252/345 |
| 5,008,103 | 4/1991 | Raleigh et al. | 424/66 |
| 5,059,704 | 10/1991 | Petroff et al. | 556/445 X |
| 5,104,998 | 4/1992 | Ichinohe | 556/445 |

FOREIGN PATENT DOCUMENTS

| | | |
|---|---|---|
| 0125779 | 11/1984 | European Pat. Off. . |
| 0310903 | 4/1989 | European Pat. Off. . |
| 3622571 | 1/1988 | Germany . |

*Primary Examiner*—Paul F. Shaver

[57] ABSTRACT

There is disclosed novel silicone polyether alkyl copolymers, and a method for their preparation, for use as emulsifiers in improved stability water-in-oil emulsions.

19 Claims, No Drawings

SILICONE POLYETHER ALKYL COPOLYMER SYNTHESIS

This is a continuation of copending application Ser. No. 07/774,444, filed on Oct. 10, 1991.

The present invention relates to novel polysiloxane-polyether copolymers and their use in stabilizing water-in-oil emulsions, such as polishes and antiperspirant compositions of the so-called dry-feeling type, comprising an emulsion of water in a volatile, water-insoluble liquid.

BACKGROUND OF THE INVENTION

A variety of polysiloxane-polyether or polysiloxane polyoxyalkylene copolymers are known in the art, and the copolymers have found many uses including the manufacture of polyurethane foams and emulsification of one of a pair of immiscible liquids in the other, such as water-in-oil, oil-in-water and oil-in-oil emulsions.

The use of polysiloxane surface active agents comprising organic polyether groups to stabilize emulsions is well known. U.S. Pat. No. 4,421,656 disclose terpolymeric polydiorganosiloxanes as stabilizers for solids-free invert emulsions for the deep well-drilling art. U.S. Pat. No. 4,254,878 uses a polysiloxane surface active agent to stabilize antiperspirant stick compositions. U.S. Pat. No. 4,218,250 uses such a polysiloxane surface active agent to stabilize polish formulations. U.S. Pat. No. 4,268,499 uses such surface active agents to stabilize antiperspirant emulsion compositions. Further, U.S. Pat. No. 4,311,695 uses such surface active agents in personal care creams and the like.

Special mention is made of U.S. Pat. No. 5,008,103, which discloses polysiloxane containing organic polyether groups. However, the polysiloxanes of the present invention have improved stability when employed with mineral oils, cyclic methylsiloxane fluids and the like in water-in-oil emulsions.

Polysiloxane surface active agents are sometimes referred to as polysiloxane-polyoxyalkylene copolymers. However, their use to date as stabilizers for silicone emulsions, particularly water-in-oil emulsions, has not always been completely satisfactory because the variables affecting their function are not well understood. Water-in-oil emulsions which contain high concentrations of salts or other ionic materials are often particularly difficult to stabilize. The problems encountered in formulating emulsions of antiperspirants in volatile fluids are exemplary of this.

Antiperspirant compositions are well known in the cosmetic art. These compositions are formulated as aerosols, gels, sticks, creams, pump sprays and lotions and comprise an astringent, typically comprising one or more zirconium salts and/or aluminum salts, in various forms such as dry, impalpable powder, an alcohol solution or an aqueous solution. Of these various forms of astringents, the aqueous solution is generally considered to be the most effective antiperspirant.

An antiperspirant composition having water as the continuous phase, such as an aqueous solution of an astringent, or an oil-in-water type emulsion thereof, is less desirable because it tends to feel wet when applied to the human skin and to go through a tacky state during the drying period after application. Therefore the use of water-in-oil emulsions to apply antiperspirants to the skin has found favor.

U.S. Pat. No. 4,122,029 discloses water-in-oil type compositions having broad utility and comprising a polydiorganosiloxane-polyoxyalkylene copolymer and a water-in-oil type surfactant. When formulated as an antiperspirant emulsion of an aqueous solution of an astringent such as aluminum chlorohydrate emulsified in a volatile, non-aqueous continuous phase, these compositions have a desirable dry feeling when applied to the human skin.

U.S. Pat. No. 4,268,499 discloses compositions described as having greater efficacy than those of U.S. Pat. No. 4,122,029. The efficacy was determined by applying compositions to subjects' wrists and measuring the time required for the composition to dry and turn white.

Another type of water-in-oil emulsion which has found favor with the public is polishes, particularly for furniture. One drawback to furniture polishes which utilize organic or organosilicone surfactants comprising long chain oxyalkylene residues, particularly long chain oxyethylene residues, is that the surfactant may tend to attack the finish of the article to be polished. This is particularly the case when the finish is based on nitrocellulose lacquers, since glycol ethers are solvents of choice for nitrocellulose finishes.

There has now been found a novel family of silicone polyether/alkyl copolymers which exhibit significant improvements in forming a wide variety of water-in-oil emulsions for use in products such as antiperspirants, hair shampoos or conditioners, hand creams, lotions, tanning oils and polishes (auto and furniture). Surprisingly, water-in-oil emulsions employing the silicone polyether copolymer emulsifiers of the present invention, exhibit significantly improved stability over prior art emulsions when emulsified with mineral oils, cyclic methyl siloxanes and other oily phase emollients.

SUMMARY OF THE INVENTION

According to the present invention there is provided a silicone polyether alkyl copolymer water-in-oil emulsifier of the general formula:

$$MD'_xD''_yM$$

wherein: M represents trimethylsiloxy endcapping units; D' represents alkyl siloxy units of the general formula $(CH_3)R'SiO_{2/2}$ where R' is an alkyl group having from 6 to about 30 carbon atoms; D" is an oxyalkylene siloxy unit of the general formula $(CH_3)R^2SiO_{2/2}$ n where $R^2$ is a polyoxyalkylene ether residue of the formula $—(R^4)_p—(OR^3)_n—OR^5$ wherein each individual $R^3$ is an alkylene radical having from 2 to 6 carbon atoms, $R^4$ is an alkylene radical having from 2 to 20 carbon atoms, $R^5$ is a hydrogen atom or a hydrocarbon radical of from 1 to about 12 carbon atoms, n has a value of from about 5 to about 20, and p has a value of zero or 1; and x is from 1 to about 29 and y is from 1 to about 29 with the proviso that x+y is from about 2 to about 30.

Preferably, x is from 1 to about 20, y is from 1 to about 20 and x+y is from about 15 to about 25. Most preferably x is 16, y is 4 and x+y is 20.

Also according to the present invention, there is provided a process for preparing the silicon polyether/alkyl copolymers of the present invention, the process comprising the following steps conducted in sequence:

(a) reacting a silicone hydride fluid of the formula $MD_qM$ (I); wherein M represents trimethylsiloxy endcapping units, D represents methylhydrosiloxy units and q represents an integer of from about 2 to about 30, with a first portion of an alpha olefin of from about 6 to about 30 carbon atoms to form a compound of the formula:

$$MD_{q-f}D'_fM \quad (II)$$

wherein M, D and q are as above defined; D' represents an alkylsiloxy unit of the formula CH$_3$R'SiO wherein R' represents an alkyl radical of from about 6 to about 30 carbon atoms and f is from about 1 to about 29;

(b) reacting a compound of formula (II) with an allyl polyether of from 2 to about 12 carbon atoms to form a compound of the formula:

$$MD_{q-r-y}D'_fD''_yM \quad (III)$$

wherein M, D, D', q and f are as above defined, and D" represents an oxyalkylene siloxy unit of the general formula (CH$_3$)R$^2$SiO$_{2/2}$ where R$^2$ is a polyoxyalkylene ether residue of the formula —(R$^4$)$_p$—(OR$^3$)$_n$—OR$^5$ wherein each individual R$^3$ is an alkylene radical having from 2 to 6 carbon atoms, R$^4$ is an alkylene radical having from 2 to 20 carbon atoms, R$^5$ is hydrogen or a hydrocarbon radical of from 1 to about 12 carbon atoms, n has a value of from about 5 to about 20, and p has a value of zero or 1, and y is from about 1 to about 29; and (c) reacting the compound of formula (III) with a second portion of said alpha olefin to form a compound of the formula:

$$MD'_xD''_yM \quad (IV)$$

wherein M, D' D" and y are as defined above, and x is from 1 to about 29 and is equal to q−y; and wherein said steps (a), (b) and (c) are carried out in the presence of a small effective amount of a catalyst for effecting said reactions.

DETAILED DESCRIPTION OF THE PRESENT INVENTION

The novel polysiloxane copolymers of the present invention are long chain hydrocarbon-modified polydiorganosiloxane polyoxyalkylene copolymers containing polydimethylsiloxy groups, on average at least one long-chain alkyl(methyl)siloxy group, and on average at least one polyoxyalkylene group, having the general formula $$MD'_xD''_yM$$

wherein:
M represents trimethylsiloxy endcapping units;
D' represents alkyl siloxy units of the general formula $$(CH_3)R'SiO_{2/2}$$

where
R' is an alkyl group having from 6 to about 30 carbon atoms;
D" is an oxyalkylene siloxy unit of the general formula $$(CH_3)R^2SiO_{2/2}$$

where

R$^2$ is a polyoxyalkylene ether residue of the formula $$-(R^4)_p-(OR^3)_n-OR^5$$

wherein
each individual R$^3$ is an alkylene radical having from 2 to 6 carbon atoms,
R$^4$ is an alkylene radical having from 2 to 20 carbon atoms,
R$^5$ is a hydrogen atom or a hydrocarbon radical of from 1 to about 12 carbon atoms,
n has a value of from about 5 to about 20, and
p has a value of zero or 1;
x is from 1 to about 29; and
y is from 1 to about 29;
with the proviso that x+y is from about 2 to about 30.

M represents hydrosiloxy endcapping units. M is generally of the formula (CH$_3$)$_2$R$^6$SiO$_{2/2}$ where R$^6$ may be an alkyl group having from 1 to 30 carbon atoms.

Preferably the radical R$^6$ of the end-blocking group M is a lower alkyl group, or else an alkyl group derived from the olefin used to form the R' groups of the D' moiety, or an R$^2$ group derived from the polyether used to form R$^2$ groups when the polysiloxane containing silicon hydride groups is end-blocked with dimethylhydrogen siloxy groups. It is preferred however to utilize a polysiloxane starting material which is end-blocked with trimethylsiloxy groups, in which case R$^6$ is methyl.

D' represents alkyl siloxy units of the general formula (CH$_3$)R'SiO$_{2/2}$ where R' is an alkyl group having from 6 to 30 carbon atoms. Preferably, R' is an alkyl group of from 8 to 18 carbon atoms, and most preferably, R' is decyl and D' is methyldecylsiloxy.

The preferred polyoxyalkylene R$^2$ segments consist solely of oxyethylene units of the formula —CH$_2$—CH$_2$O—, i.e. R$^3$ is ethylene. It further important herein that the number of repeating units of —OR$^3$—, i.e., the value of n, be between about 5 and about 20. Thus, in the case of ethylene oxide as the repeating unit, the molecular weight of R$^2$ should be less than about 900. The preferred value of n is from 10 to 15, which likewise for ethylene oxide provides a molecular weight for R$^2$ of no more that about 700.

R$^4$ is the group which bonds the polyoxyalkylene segment to the polysiloxane. R$^4$ may be —CH$_2$CH$_2$CH$_2$—, —CH$_2$CH$_2$—, —CH$_2$CH$_2$CH$_2$CH$_2$—, etc. Preferably, R$^4$ is —CH$_2$CH$_2$CH$_2$—. When "p" is zero, the segments are joined by —O— which is the product of a condensation reaction between a condensable substituent on the polysiloxane and a condensable end group on the polyalkylene oxide. Although the compositions of the present invention are not soluble in water, and therefore not subjected to vigorous hydrolysis conditions in emulsions employing the compositions of the present invention, it is preferred that "p" be 1, avoiding the use of the hydrolyzable carbon-oxygen-silicon bond to link the polyoxyalkylene residue to the polysiloxane chain.

R$^5$ is the terminal group of the polyalkylene ether. The type of R$^5$ is not critical and may be selected from hydrogen, methyl, ethyl, propyl, butyl, phenyl, acetyl, etc. Preferably R$^5$ is hydrogen.

A particularly preferred alkyl siloxy unit D" is methyl polyethoxy siloxy having an average R$^2$ molecular weight of from about 300 to about 800.

The copolymers of the present invention have values for x and y which are independently each from 1 to about 29 and are required to add up, x+y, to from about 2 to about 30. Preferably x and y are each independently from 1 to about 20 and x+y is from about 15 to about 25. Most preferably x is 16 and y is 4.

The present invention is also directed to a novel method for forming the silicon polyether alkyl copolymers of the present invention. The novel method comprises the following steps conducted in sequence:

(a) reacting a silicone hydride fluid of the formula $$MD_qM \qquad (I)$$

wherein:

M represents trimethylsiloxy endcapping units,
D represents methylhydrosiloxy units and
q represents an integer of from about 2 to about 30,
with a first portion of an alpha olefin of from about 6 to about 30 carbon atoms to form a compound of the formula:

$$MD_{q-f}D'_fM \qquad (II)$$

wherein:

M, D and q are as above defined;
D' represents an alkylmethylsiloxy unit of the formula $$CH_3R'SiO$$

wherein R' represents an alkyl radical of from about 6 to about 30 carbon atoms; and
f is from about 1 to about 29;

(b) reacting a compound of formula (II) with an allyl polyether of from 2 to about 12 carbon atoms to form a compound of the formula:

$$MD_{q-f-y}D'_fD''_yM \qquad (III)$$

wherein:

M, D, D', q and f are as above defined, and
D" represents an oxyalkylene siloxy unit of the general formula $$(CH_3)R^2SiO_{2/2}$$

where
R² is a polyoxyalkylene ether residue of the formula $$-(R^4)_p-(OR^3)_n-OR^5$$

wherein
each individual R³ is an alkylene radical having from 2 to 6 carbon atoms,
R⁴ is an alkylene radical having from 2 to 20 carbon atoms,
R⁵ is hydrogen or a hydrocarbon radical of from 1 to about 12 carbon atoms,
n has a value of from about 5 to about 20,
p has a value of zero or 1, and
y is from about 1 to about 29; and (c) reacting the compound of formula (III) with a second portion of said alpha olefin to form a compound of the formula:

$$MD'_xD''_yM \qquad (IV)$$

wherein:

M, D' D" and y are as defined above, and
x is from 1 to about 29 and is equal to q−y; and
wherein said steps (a), (b) and (c) are carried out in the presence of a small effective amount of a catalyst for effecting said reactions.

The method for preparing the polydiorganosiloxane component generally comprises reacting a methyl siloxane having terminal and/or in-chain silicon-bonded hydrogen atoms with a first portion of an olefin having from 6 to 30 carbon atoms, such as 1-octene, 1-decene, 1-octadecene or -dodecene, then with an olefinically terminated polyoxyalkylene, such as polyoxyethylene, and then with a second portion of the alpha olefin, all in the presence of an effective amount of a platinum-containing catalyst, such as a chloroplatinic acid, i.e. $H_2PtCl_6.6H_2O$. In this method the first portion of olefin, the olefinically terminated polyoxyalkylene, and the second portion of olefin are reacted sequentially, first portion of olefin first, with the methylsiloxane containing silicon-bonded hydrogen radicals. It is to be understood that the polydiorganosiloxanes that have been prepared in this preferred manner can contain small amounts of unreacted olefin and/or olefin-terminated polyoxyalkylene.

Any catalyst known to those skilled in the art for effecting the copolymerization reactions of the present invention may employed herein. These catalysts are described in the literature, e.g., Lamoreaux, U.S. Pat. No. 3,220,972. Platinum based catalysts are preferred. Preferably the amount of catalyst is present in an amount ranging from about 0.05 to 0.5 weight percent based on the weight of the starting hydrogen silicon hydride.

In preferred embodiments, the first and second portions of the alpha olefin represent substantially equivalent amounts of the same alpha olefin. Most preferably the alpha olefin is 1-decene and the allyl polyether is an allyl initiated all ethylene oxide polyether, hydroxy capped of average 550 molecular weight.

The silicon polyether alkyl copolymers of the present invention can be used as emulsifiers to form the novel water-in-oil emulsions of the present invention. The novel water-in-oil emulsions of the present invention generally comprise (A) from about 10 to about 50. parts by weight of an oily phase; (B) from about 40 to about 80 parts by weight of a discontinuous phase and (C) from about 1 to about 15 parts by weight the silicon polyether alkyl copolymer emulsifiers of the present invention.

Component A of the water-in-oil emulsions of the present invention can comprise a wide variety of emollients, such as paraffinic hydrocarbon liquids, mineral oils and petrolatum. These are well known in the chemical and polymer arts and are available commercially.

The oily phase may also comprises a volatile liquid having a normal boiling point less than 250° C., the volatile liquid being selected from methylsiloxane fluids having the average unit formula $(CH_3)_aSiO_{(4-a)/2}$ wherein a has an average value of from 2 to 3 inclusive. Preferred siloxane units are selected from the group consisting of $(CH_3)_3SiO_{1/2}$, $(CH_3)_2SiO_{2/2}$, $CH_3SiO_{3/2}$ and $SiO_{4/2}$ units. Preferably, the volatile methylsiloxane fluid consists essentially of dimethylsiloxane units, and optionally, trimethylsiloxane units. Of particular value as volatile liquid (A) are the cyclic siloxanes of the general formula $((CH_3)_2SiO)_b$ and the linear siloxanes of the general formula $(CH_3)_3SiO((CH_3)_2SiO)_cSi(CH_3)_3$, and their mixtures, wherein b is an integer of from 3 to 6 and C is an integer of from 0 to 4. A highly preferred methylsiloxane fluid is a mixture of said cyclic siloxanes wherein a major portion is tetramer (b=4 or 5).

Component B of the water-in-oil emulsions of the present invention is the discontinuous phase. Most preferably the discontinuous phase comprises water.

However, it is also contemplated that the discontinuous phase comprises liquid media other than water. Suitable other liquid media are organic compounds such as alcohols, including methanol, ethanol, phenol, ethylene glycol, propylene glycol, glycerine, their partial ethers and partial esters; nitrogen compounds including amides such as formamide, acetamide, N,N-dimethyl formamide and urea; nitriles such as acetonitrile, and amines and their salts; acids such as formic acid, acetic acid, benzoic acid, stearic acid and ethylene diaminetetraacetic acid; and ethers such as furan, tetrahydrofuran, dioxane, ethylene glycol dimethyl ether, propylene glycol dimethyl ether and their polymeric forms such as triethylene glycol diethyl ether. Mixtures of any of the foregoing and mixtures of any of them with water are contemplated by the present invention.

Emulsion compositions of this invention wherein the aqueous phase comprises water and/or ethanol are particularly useful. In common with oil-in-water emulsions, water-in-oil emulsions are desirable from an economic, safety and environmental viewpoint as a means of preparing, storing, shipping and using efficacious components. In addition, emulsion compositions of aqueous or ethanol solutions have value as personal care compositions.

It is further contemplated that the aqueous phase can comprise small amounts of additives, such as electrolytes, incorporated therein. Preferred is from about 0.5 to about 5 parts by weight of sodium chloride.

The emulsions of the present invention may also comprise a wide variety of efficacious additives (D) for imparting desired characteristics on the emulsions depending upon the end use. Preferred additives are selected from the group consisting of an antiperspirant, a humectant, an insect repellent, an odorant, a deodorant, an emollient, an antiseptic, a sunscreen, a cleansing agent, a suitable pharmaceutical, a pigment, a biocide and mixtures of any of the foregoing.

Preferred are sunscreens such as titanium dioxide and UVA and UVB type sunblocks. These and others are well known to those skilled in the art and are available commercially. Preferably the type and amount of sunscreen additives are sufficient to provide a sun protection factor of greater than 10, most preferably at least about 15.

Also preferred are antiperspirant additives. Preferably the antiperspirant additive is a water soluble astringent antiperspirant agent. Examples of well known astringents include aluminum, hafnium and zirconium salts, such as zirconyl hydroxide halides, aluminum zirconium chloride, zirconium-aluminum lactate, basic aluminum halides such as $Al_2(OH)_5Cl$, aluminum bromide and the several water, alcohol or glycine complexes thereof.

The amount of astringent that is employed may vary widely and is not critical; however, certain practical limitations exist. On the one hand an efficacious antiperspirant composition would contain sufficient astringent to provide sweat reduction, although compositions containing less astringent are useful as personal care compositions. Preferably, the antiperspirant composition comprises approximately 15-30 weight percent astringent. On the other hand, it is desirable to maximize the amount of water in the antiperspirant formulation without negating utility, for obvious economic reasons. Depending on the particular astringent used, the amount of astringent may vary in concentration in the aqueous phase from as little as one part by weight astringent per three parts by weight water up to a saturated aqueous solution of the astringent.

The emulsions of the present invention are suitable for use, without further processing, as a lotion, preferably packaged and dispersed as a roll-on antiperspirant composition. However, gel, aerosol and pump spray formulations may be prepared therefrom using well known adjuvants such as alcohols for gel formation and solvents to reduce the viscosity of the formulation less than 100 centipoise at 25° C. for aerosol and pump spray use.

The emulsions of the present invention may be prepared by mixing the proper portions of the individual components in any order. Although the compositions of the invention are delineated in terms of an aqueous solution (A) emulsified in a volatile liquid (B) using an emulsifier (C), the emulsions can be formed by preparing an aqueous phase, and by preparing an oily phase comprising the volatile liquid (B) and the emulsifier (C), and thereafter mixing the aqueous phase and the oily phase. Mixing may be done using standard emulsifying methods. Optionally, the emulsions may be further homogenized. It is also contemplated that a second conventional emulsifier may be added.

The additive (D) is added either to the aqueous phase, as in the case of astringents, or to the oily phase, as in the case of sunscreens, depending upon the type of additives as known to those skilled in the art.

The amounts of components (A) and (B) that may be present in the emulsion compositions of the present invention may vary widely, and generally comprise, in total, from about 99.5 to about 91 percent by weight of the total weight of components (A) through (C).

It is also contemplated that the emulsions of the present invention can be formulated into solid compositions, such as antiperspirant sticks. The solid forms of the emulsions of the present invention are generally prepared by the addition of an organic wax.

Suitable organic waxes include mineral waxes, such as paraffin, etc.; vegetable waxes, such as carnauba, flax, candelilla, etc.; and animal waxes such as bees wax. Chemically these waxes are branched or straight chain hydrocarbons, high molecular weight fatty acids, high molecular weight alcohols, or high molecular weight fatty acid esters. Characteristically waxes have low viscosities just above their melting point. For use herein, the waxes should have a melting point between about 40° and 65° C. Such a melting point allows for proper application rates and prevents melting upon storage under ambient conditions. Preferably the organic wax is a mixture of waxes to control the hardness of the stick composition. Thus, a preferred organic wax is a mixture of a waxy ester for hardness, such as methyl hydroxystearate, and a solid alkanol such as stearyl alcohol. Where such a mixture of waxes is used, the organic wax might contain 10 to 50 percent by weight solid alkanol and 50 to 90 weight percent waxy ester. Hardness is also greatly effected by the proportion of organic wax in the stick composition. Preferably, the continuous oil matrix contains about 25 to 40 percent by weight organic wax.

The antiperspirant stick is easily prepared by methods well known in the art. Herein, the methylsiloxane fluid, organic wax and emulsifier of the present invention are all heated until all components are liquid and then mixed. Generally the components will liquify between about 40° and 70° C. Subsequently, the water solution with active ingredient is warmed and emulsified into the molten wax as is known. The warm emulsion is poured as close to solidification temperature as possible into molds and allowed to cool. The solid stick compositions containing the emulsifiers of the present invention have improved stability over those described in the prior art, are drier and do not require the addition of other surfactants although other surfactants can be employed if desired.

The emulsions of the present invention may further comprise small amounts of non-essential components which are commonly used in the cosmetic art. Examples of such components include colorants; perfumes; viscosity control additives such as solvents or thickening agents for the continuous phase; and non-volatile organopolysiloxanes, such as polydimethylsiloxanes having a viscosity of from 10 to 10,000 centipoise at 25° C. In the case of antiperspirant sticks, talc may be preferably added. These additives may be added in greater or lesser amounts, depending on the needs of the individual user.

DESCRIPTION OF THE PREFERRED EMBODIMENTS

The following examples illustrate the present invention. They are not to be construed to limit the scope of the appended claims in any manner whatsoever.

EXAMPLE 1

To a 3 liter pot is added 235 grams of hydride siloxane with average structure $MD_{20}M$ and 385 grams of toluene. The mixture is azeotroped dry.

At 100° C., Pt catalyst (3% platinum content, chloroplatinic acid, See, U.S. Pat. No. 3,220,972) was added (0.4 grams). To this is added 193 grams of decene-1 (½ the total amount) controlling the exotherm at 100°–120° C.

Following the addition of decene-1, the mixture is cooled to less than 70° C. To the cooled mixture is then added 10 grams of 0.2μ sodium acetate buffer solution. The mixture is then heated back to 90°–100° C.

At 100° C., 879 grams of a 50/50 mix of toluene and allyl initiated all ethylene oxide polyether, hydroxy capped of average 550 molecular weight is added over a hour period.

At the end of the allyl polyether addition, another 193 grams of decene-1 is added to complete the reaction.

The entire reaction product is stripped to pot temperature of 130° C. under nitrogen vacuum of 10 mm. The product is then filtered through Celite 545 diatomaceous earth (Johns Manville).

EXAMPLE 2

The emulsifier prepared in Example 1 is employed in a water-in-oil emulsion. First the oil phase is prepare by mixing 17.0 parts by weight of a heavy mineral oil, 3.0 parts by weight of SF-1202 (a cyclomethyl siloxane fluid, General Electric Company), and 2.0 parts by weight of the emulsifier of Example 1.

Second, the aqueous phase is prepared by mixing together 3.0 parts by weight of propylene glycol, 1.0 part by weight of sodium chloride and 74.0 parts by weight of water.

The oily phase is then added to the aqueous phase with high shear agitation. The emulsion formed is then milled in a Gifford-Wood homogenizer to increase stability. The resulting emulsion passed stability testing: 60 days at 40° C. and 4 freeze/thaw cycles.

EXAMPLE 3

An emulsion is prepared in the same procedure as in Example 2, except the oily and aqueous phases are varied. The oily phase comprises: 9.0 parts by weight of a light mineral oil; 6.0 parts by weight of isopropyl myristate, 3.0 parts by weight of petrolatum; and 2.5 parts by weight of the emulsifier of Example 1. The aqueous phase comprises: 5.0 parts by weight of glycerine, 1.0 part by weight of sodium chloride and 73.5 parts by weight of water.

The emulsion formed is found to pass stability tests for 60 days at 40° C., and 4 freeze/thaw cycles.

EXAMPLE 4

The emulsifier prepared in claim 1 is employed in a water-in-oil sunscreen emulsion. The emulsion is prepared in the same manner as the emulsions of claim 2. The oily phase consists of 7.5 parts by weight of 2-ethylhexyl p-methoxycinnamate (a UVB sunscreen); 5.0 parts by weight of menthyl-o-aminobenzoate (a UVA sunscreen); 3.0 parts by weight of isopropyl myristate (an emollient); 4.0 parts by weight of mineral oil, 55-70 SUS (an emollient); 5.0 parts by weight of SF-1202 (an emollient—cyclomethyl siloxane fluid, General Electric Company); and 2.0 parts by weight of the emulsifier of claim 1.

The aqueous phase consists of 3.5 parts by weight of glycerine (a humectant); 1.0 parts by weight of sodium chloride (an electrolyte); and 69.0 parts by weight of water (a diluent).

The resulting emulsion passed 60 days at 40° C stability testing. The resulting emulsion also passed stability testing at 4 freeze/thaw cycles.

EXAMPLE 5

The procedure of Example 4 is repeated to prepare a different water-in-oil sunscreen.

The oily phase consists of: 7.5 parts by weight of 2-ethylhexyl p-methoxycinnamate (UVB sunscreen); 5.0 parts by weight of menthyl-o-aminobenzoate (UVA sunscreen); 3.0 parts by weight of isopropyl myristate (emollient); 4.0 parts by weight of mineral oil, 55-70 SUS (emollient); 7.0 parts by weight of SF-1202 (emollient—cyclomethyl siloxane fluid, General Electric Company); and 2.5 parts by weight of the emulsifier of claim 1.

The aqueous phase consists of 3.0 parts by weight of glycerine (humectant); 1.5 parts by weight of sodium chloride (electrolyte); and 66.5 parts by weight of water (a diluent).

The resulting emulsion passed 60 days at 40° C. stability testing. The resulting emulsion also passed stability testing at 4 freeze/thaw cycles. The statis SPF of the sunscreen was 9.8 when tested on 6 humans by standard SPF determination of sun protection products.

EXAMPLE 6

A water-in-oil sunscreen is prepared according to the procedure of Example 4 with a varied formulation.

The oily phase consists of: 7.5 parts by weight of 2-ethylhexyl p-methoxycinnamate (UVB sunscreen); 5.0 parts by weight of titanium dioxide (UVA/UVB sunblock); 4.0 parts by weight of isopropyl palmitate (emollient); 5.0 parts by weight of mineral oil, 55-70 SUS (emollient); 5.0 parts by weight of SF1202 (emollient—cyclomethyl siloxane fluid, General Electric Company); and 2.0 parts by weight of the emulsifier of claim 1.

The aqueous phase consists of 3.0 parts by weight of propylene glycol (humectant); 1.0 parts by weight of sodium chloride (electrolyte); and 67.5 parts by weight of water (a diluent).

The resulting emulsion passed 60 days at 40° C stability testing. The resulting emulsion also passed stability testing at 4 freeze/thaw cycles.

EXAMPLES 7-8

Two water-in-oil sunscreens are prepared according to the procedure of Example 4. The compositional data for the two emulsions are set forth below in Table 1.

TABLE 1

| Example | 7 | 8 | Function |
|---|---|---|---|
| Oily phase | | | |
| 2-Ethylhexyl p-methoxycinnamate | 7.5 | 7.5 | UVB sunscreen |
| 2-Hydroxy-4-methoxybenzophenone | 3.0 | 3.0 | UVA/UVB sunscreen |
| Isopropyl myristate | 6.0 | 7.0 | Emollient |
| Mineral Oil (55-70 SUS) | 6.0 | 6.0 | Emollient |
| SF1202[a] | 2.0 | 3.0 | Emollient |
| Ganex V-220[b] | — | 2.0 | Film former |
| Titanium dioxide | — | 3.0 | UVA/UVB sunscreen |
| Emulsifier[c] | 2.5 | 2.5 | Emulsifier |
| Aqueous Phase | | | |
| Propylene glycol | 3.0 | 3.0 | Humectant |
| Sodium chloride | 1.5 | 1.5 | Electrolyte |
| Water | 68.5 | 61.5 | Diluent |

[a]Cyclomethyl siloxane fluid, General Electric Company
[b]PVP/EICOSENE Copolymer, GAF Corporation
[c]Copolymeric emulsifier of Example 1

Both formulations, Examples 7 and 8, passed 60 days at 40° C. stability testing. The formulation of Example 7 was static tested for SPF on six humans by standard SPF determination of sun protection products. The resulting SPF obtained was 15.3.

EXAMPLE 9

The procedure of Example 4 was followed, varying the formulation, to prepare a sunscreen water-in-oil emulsion.

The oily phase consisted of: 7.5 parts by weight of 2-ethylhexyl p-methoxycinnamate (UVB sunscreen); 4.0 parts by weight of 2-ethylhexyl salicylate (UVB sunscreen); 2.0 parts by weight of 2-hydroxy-4-methoxybenzophenone (UVA/UVB sunscreen); 8.0 parts by weight of myristyl propionate (emollient); 7.0 parts by weight of SF1202 (emollient—cyclomethyl siloxane fluid, General Electric Company); and 2.5 parts by weight of the emulsifier of Example 1.

The aqueous phase consisted of 3.0 parts by weight of propylene glycol (humectant); 1.5 parts by weight of sodium chloride (electrolyte); and 64.5 parts by weight of water (diluent).

The sunscreen emulsion passed 60 days at 40° C. stability testing, and passed stability testing at 4 freeze/thaw cycles.

The above mentioned patents and publications are incorporated herein by reference.

Many variations of the present invention will suggest themselves to those skilled in this art in light of the above detailed description. All such obvious modifications are within the full intended scope of the appended claims.

We claim:

1. A silicone polyether alkyl copolymer water-in-oil emulsifier of the general formula:

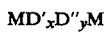

wherein
M represents trimethylsiloxy endcapping units;
D' represents alkyl siloxy units of the general formula $(CH_3)R'SiO_{2/2}$ where R' is an alkyl group having from 6 to 30 carbon atoms;
D" is an oxyalkylene siloxy unit of the general formula $(CH_3)R^2SiO_{2/2}n$ where $R^2$ is a polyoxyalkylene ether residue of the formula $—(R^4)_p—(OR^3—)_n—OR^5$ wherein each individual $R^3$ is an alkylene radical having from 2 to 6 carbon atoms, $R^4$ is an alkylene radical having from 2 to 20 carbon atoms, $R^5$ is hydrogen or a hydrocarbon radical of from 1 to about 12 carbon atoms, n has a value of from about 5 to about 20, and p has a value of zero or 1,
x is from 1 to about 29, and
y is from 1 to about 29;
with the proviso that x+y is from about 2 to about 30.

2. A copolymer as defined in claim 1, wherein R' is an alkyl group of from about 8 to about 18 carbon atoms.

3. A copolymer as defined in claim 2, wherein R' is and alkyl group of 10 carbon atoms and D' represents methyl decylsiloxy units.

4. A copolymer as defined in claim 1, wherein D" represents methyl polyethoxy siloxy units.

5. A copolymer as defined in claim 1, wherein D" has an average $R^2$ molecular weight of from about 300 to about 800.

6. A copolymer as defined in claim 1, wherein x is from 1 to about 20, y is from 1 to about 20 and x+y is from about 15 to about 25.

7. A copolymer as defined in claim 6, wherein x is about 16, y is about 4 and x+y is about 20.

8. A copolymer as defined in claim 1, wherein D' represents methyl decylsiloxy units, D" represents methyl polyethoxy siloxy units and x+y is about 20.

9. A water-in-oil emulsion comprising:
(A) from about 10 to about 50 parts by weight of an oily phase;
(B) from about 40 to about 80 parts by weight of a discontinuous phase; and
(C) from about 1 to about 15 parts by weight the silicon polyether alkyl copolymer emulsifiers as defined in claim 1.

10. A water-in-oil emulsion as defined in claim 9 wherein said oily phase (A) comprises an oil selected from the group consisting of mineral oils, petrolatum, paraffinic hydrocarbon liquids and mixtures of any of the foregoing.

11. A water-in-oil emulsion as defined in claim 9, wherein said oily phase comprises a volatile liquid having a normal boiling point of less than 250° C. said volatile liquid being selected from the group consisting of methylsiloxane fluids having the average unit formula

wherein a has an average value of from 2 to 3 inclusive.

12. A water-in-oil emulsion as defined in claim 11 wherein said volatile methylsiloxane fluid consists essentially of dimethylsiloxane units.

13. A water-in-oil emulsion as defined in claim 12 wherein said methylsiloxane fluids are cyclic siloxanes of the general formula $((CH_2)SiO)_b$ wherein b is an integer of from 3 to 6.

14. A water-in-oil emulsion as defined in claim 9, wherein said aqueous phase (B) comprises water.

15. A water-in-oil emulsion as defined in claim 9 further comprising (D) an effective amount of an efficacious additive.

16. A water-in-oil emulsion as defined in claim 15, wherein said additive is selected from the group consisting of an antiperspirant, a humectant, an insect repellent, an odorant, a deodorant, an emollient, an antiseptic, a sunscreen, a cleansing agent, a suitable pharmaceutical, a pigment, a biocide and mixtures of any of the foregoing.

17. A water-in-oil emulsion as defined in claim 16 wherein said additive comprises a sunscreen.

18. A water-in-oil emulsion as defined in claim 16 wherein said additive comprises an antiperspirant selected from water soluble astringents.

19. A water-in-oil emulsion as defined in claim 18 in the form of stick further comprising an organic wax.

* * * * *